(12) United States Patent
Wang et al.

(10) Patent No.: US 11,096,780 B2
(45) Date of Patent: Aug. 24, 2021

(54) PARAVALVULAR LEAK RESISTANT PROSTHETIC HEART VALVE SYSTEM

(71) Applicant: Medtronic, Inc., Minneapolis, MN (US)

(72) Inventors: Wei Wang, Garden Grove, CA (US); Joshua Dudney, Mission Viejo, CA (US); Kshitija P. Garde, Irvine, CA (US); Laura McKinley, Costa Mesa, CA (US); Benjamin Wong, Irvine, CA (US)

(73) Assignee: Medtronic, Inc., Minneapolis, MN (US)

( * ) Notice: Subject to any disclaimer, the term of this patent is extended or adjusted under 35 U.S.C. 154(b) by 197 days.

(21) Appl. No.: 16/407,321

(22) Filed: May 9, 2019

(65) Prior Publication Data

US 2019/0269504 A1 Sep. 5, 2019

Related U.S. Application Data

(62) Division of application No. 14/259,340, filed on Apr. 23, 2014, now Pat. No. 10,321,987.

(51) Int. Cl.
*A61F 2/24* (2006.01)
*A61L 27/20* (2006.01)
*A61L 27/50* (2006.01)

(52) U.S. Cl.
CPC .............. *A61F 2/2409* (2013.01); *A61F 2/24* (2013.01); *A61F 2/2412* (2013.01); *A61F 2/2418* (2013.01); *A61L 27/20* (2013.01); *A61L 27/50* (2013.01); *A61L 27/507* (2013.01); *A61F 2/2436* (2013.01); *A61F 2210/0061* (2013.01); *A61F 2250/0069* (2013.01); *A61L 2430/20* (2013.01)

(58) Field of Classification Search
CPC .... A61F 2/24; A61F 2/2418; A61F 2002/077; A61F 2210/0061
See application file for complete search history.

(56) References Cited

U.S. PATENT DOCUMENTS

| | | | |
|---|---|---|---|
| 5,957,949 | A | 9/1999 | Leonhardt et al. |
| 8,052,750 | B2 | 11/2011 | Tuval et al. |
| 8,801,768 | B2 | 8/2014 | Karwa et al. |
| 2004/0111111 | A1 | 6/2004 | Lin |
| 2005/0137688 | A1 | 6/2005 | Salahieh et al. |
| 2006/0265056 | A1 | 11/2006 | Nguyen et al. |

(Continued)

FOREIGN PATENT DOCUMENTS

CA 2703807 11/2011

OTHER PUBLICATIONS

PCT/US2015/024557, The International Search Report and Written Opinion of the ISA, dated Jun. 23, 2015.

*Primary Examiner* — Bruce E Snow
(74) *Attorney, Agent, or Firm* — Dicke, Billig & Czaja, PLLC

(57) ABSTRACT

A paravalvular leak resistant prosthetic heart valve system including a stent frame, a valve structure and a sealing mechanism. The stent frame has a surface. The valve structure is associated with the stent frame. The sealing mechanism at least partially extends over the surface of the stent frame. The sealing mechanism includes at least one semi-permeable membrane and an osmotic gradient driving material.

15 Claims, 4 Drawing Sheets

(56) References Cited

U.S. PATENT DOCUMENTS

| | | |
|---|---|---|
| 2007/0239266 A1 | 10/2007 | Birdsall |
| 2007/0239269 A1 | 10/2007 | Dolan et al. |
| 2012/0303116 A1 | 11/2012 | Gorman, III et al. |
| 2013/0172490 A1 | 7/2013 | Way et al. |
| 2013/0274873 A1 | 10/2013 | DeLaloye |
| 2013/0331929 A1* | 12/2013 | Mitra ............... A61F 2/2418 623/2.11 |
| 2015/0272732 A1* | 10/2015 | Tilson ............. A61M 25/1029 623/2.11 |
| 2020/0046495 A1* | 2/2020 | Gorman, III ......... A61F 2/2436 |

* cited by examiner

PARAVALVULAR LEAK RESISTANT PROSTHETIC HEART VALVE SYSTEM

CROSS-REFERENCE TO RELATED APPLICATIONS

This application is a Division of U.S. patent application Ser. No. 14/259,340, filed Apr. 23, 2014, entitled "Paravalvular Leak Resistant Prosthetic Heart Valve System", the entire teachings of which are incorporated herein by reference.

BACKGROUND

The present disclosure relates to systems and methods of reducing leakage around a medical implant. More particularly, the invention relates to a paravalvular leak resistant prosthetic heart valve system.

A human heart includes four heart valves that determine the pathway of blood flow through the heart: the mitral valve, the tricuspid valve, the aortic valve, and the pulmonary valve. The mitral and tricuspid valves are atrioventricular valves, which are between the atria and the ventricles, while the aortic and pulmonary valves are semilunar valves, which are in the arteries leaving the heart. Ideally, native leaflets of a heart valve move apart from each other when the valve is in an open position, and meet or "coapt" when the valve is in a closed position. Problems that may develop with valves include stenosis in which a valve does not open properly, and/or insufficiency or regurgitation in which a valve does not close properly. Stenosis and insufficiency may occur concomitantly in the same valve. The effects of valvular dysfunction vary, with regurgitation or backflow typically having relatively severe physiological consequences to the patient.

Diseased or otherwise deficient heart valves can be repaired or replaced with an implanted prosthetic heart valve. Conventionally, heart valve replacement surgery is an open heart procedure conducted under general anesthesia, during which the heart is stopped and blood flow is controlled by a heart-lung bypass machine.

Traditional open heart surgery inflicts significant patient trauma and discomfort, and exposes the patient to a number of potential risks, such as infection, stroke, renal failure, and adverse effects associated with the use of the heart-lung bypass machine, for example.

Due to the drawbacks of open-heart surgical procedures, there has been an increased interest in minimally invasive replacement of cardiac valves. Recently, prosthetic valves supported by stent frame structures that can be delivered percutaneously using a catheter-based delivery system have been developed for heart and venous valve replacement. With these percutaneous transcatheter (or transluminal) techniques, a valve prosthesis is compacted for delivery via a catheter and then advanced, for example, through an opening in the femoral artery and through the descending aorta to the heart, where the prosthesis is then deployed in the annulus of the valve to be repaired (e.g., the aortic valve annulus).

Percutaneously delivered prosthetic valves may include either self-expandable, balloon-expandable, and/or mechanically-expandable stent frame structures with a valve structure attached or coupled to the interior of the stent frame structure. The prosthetic valve may be reduced in diameter, by crimping onto a balloon catheter or by being contained within a sheath component of a delivery catheter, and advanced through the venous or arterial vasculature. Once the prosthetic valve is positioned at the treatment site, for instance within an incompetent native valve, the stent frame structure may be expanded to hold the prosthetic valve firmly in place. One example of a stented prosthetic valve is disclosed in U.S. Pat. No. 5,957,949 to Leonhardt et al., which is incorporated by reference herein in its entirety.

Although transcatheter techniques have attained widespread acceptance with respect to the delivery of conventional stents to restore vessel patency, only mixed results have been realized with percutaneous delivery of a relatively more complex prosthetic heart valve.

Various types and configurations of prosthetic heart valves are available, and continue to be refined. The actual shape and configuration of any particular prosthetic heart valve is dependent to some extent upon native shape and size of the valve being repaired (i.e., mitral valve, tricuspid valve, aortic valve, or pulmonary valve). In general, prosthetic heart valve designs attempt to replicate the functions of the valve being replaced and thus may include a valve structure comprising one or more leaflet-like structures.

With a bioprosthesis construction, the replacement valve may include a valved vein segment that is mounted in some manner within an expandable stent frame to make a valved stent (or "stented prosthetic heart valve"). For many percutaneous delivery and implantation systems, the self-expanding valved stent is crimped down to a desired size and held in that compressed state within an outer sheath, for example. Retracting the sheath from the valved stent allows the stent to self-expand to a larger diameter, such as when the valved stent is in a desired position within a patient.

In other percutaneous implantation systems, the valved stent can be initially provided in an expanded or uncrimped condition, then compressed or crimped on a balloon portion of a catheter until it is as close to the diameter of the catheter as possible. Once delivered to the implantation site, the balloon is inflated to deploy the so-configured prosthesis. With either of these types of percutaneous stent delivery systems, conventional sewing of the prosthetic heart valve to the patient's native tissue is typically not necessary.

It is imperative that the stented prosthetic heart valve be accurately positioned relative to the native valve immediately prior to deployment from the catheter as successful implantation requires the transcatheter prosthetic heart valve intimately lodge and seal against the native tissue. If the prosthesis is incorrectly positioned relative to the native tissue, serious complications can result as the deployed device can leak and may even dislodge from the implantation site.

Even when the stented prosthetic heart valve is accurately positioned in the native valve, at least a portion of the annulus may have an irregular shape, which impacts the ability to form a good seal between the stented prosthetic heart valve and the native valve.

Leaking of blood around an implanted prosthetic heart valve is referred to as a paravalvular leak, which can lead to heart failure and increase risk of infectious endocarditis.

In light of the above, although there have been advances in percutaneous valve replacement techniques and devices, there is a continued desire to provide enhanced sealing between the prosthetic heart valve and the native valve.

SUMMARY

An embodiment of the invention is directed to a paravalvular leak resistant prosthetic heart valve system that includes a stent, a valve structure and a sealing mechanism. The stent frame has a surface. The valve structure is associated with the stent frame. The sealing mechanism at least partially extends over the surface of the stent frame. The sealing mechanism includes at least one semi-permeable membrane and at least one osmotic gradient driving material.

Another embodiment of the invention is directed to a method of reducing paravalvular leakage from a prosthetic heart valve. A prosthetic heart valve is provided that includes a stent frame having a surface, a valve structure associated with the stent frame, a sealing mechanism comprising at least one semi-permeable membrane and at least one osmotic material driving compound. The sealing mechanism is positioned at least partially over the surface of the stent frame. The prosthetic heart valve is deployed in a patient. The osmotic gradient driving material causes fluid of the patient to pass through the at least one semi-permeable membrane. The fluid that passes through the at least one semi-permeable membrane causes the sealing mechanism to swell and such swelling reduces paravalvular leakage between the prosthetic heart valve and tissue of the patient.

DETAILED DESCRIPTION

Figure 1A:
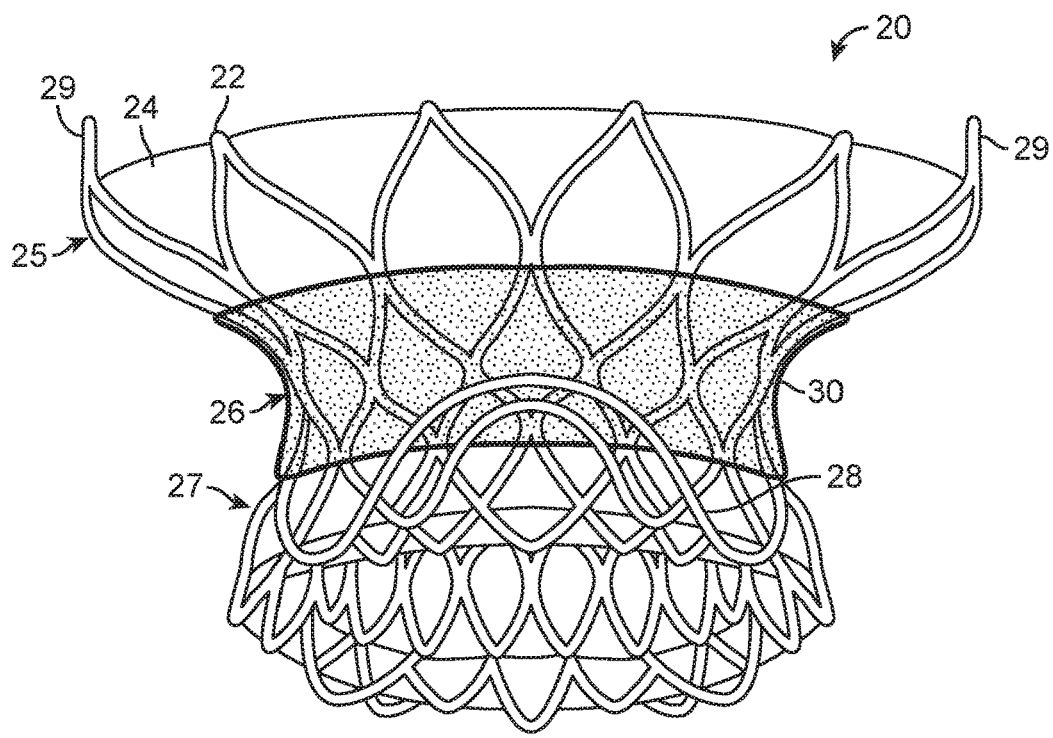
FIG. 1a is a side view of paravalvular leakage resistant prosthetic heart valve according to an embodiment of the invention.

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician. As used herein with reference to an implanted valve prosthesis, the terms "distal," "outlet" and "outflow" are understood to mean downstream to the direction of blood flow, and the terms "proximal," "inlet" or "inflow" are understood to mean upstream to the direction of blood flow. In addition, as used herein, the terms "outward" or "outwardly" refer to a position radially away from a longitudinal axis of a frame of the valve prosthesis and the terms "inward" or "inwardly" refer to a position radially toward a longitudinal axis of the frame of the valve prosthesis. As well the terms "backward" or "backwardly" refer to the relative transition from a downstream position to an upstream position and the terms "forward" or "forwardly" refer to the relative transition from an upstream position to a downstream position.

The invention is directed to a system and method for sealing a prosthetic heart valve or other implanted tissue with respect to a native valve in which the prosthetic heart valve is placed. The invention thereby reduces the potential value of a paravalvular leak and the associated complications resulting therefrom.

The system 10 includes a prosthetic heart valve 20 and an associated sealing mechanism 30, as illustrated in the figures. In general terms, the prosthetic heart valves 20 of the present disclosure include a valve structure (tissue or synthetic) 24 mounted with respect to a stent or stent frame 22, as illustrated in FIGS. 1a, 1b and 2.

Figure 1B:
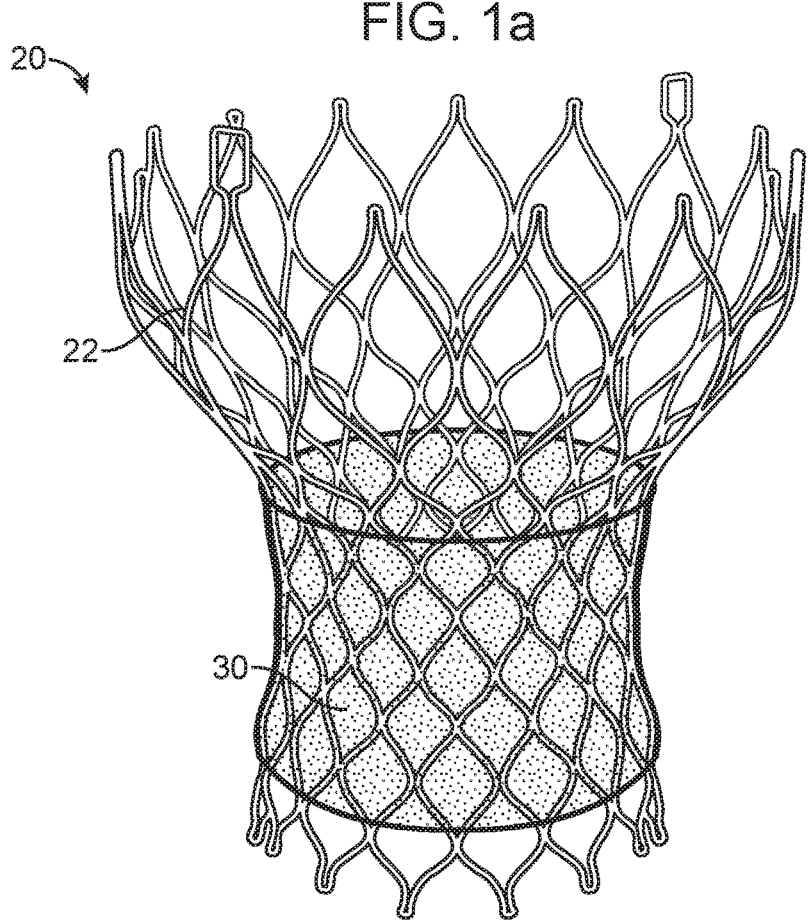
FIG. 1b is a side view of paravalvular leakage resistant prosthetic heart valve according to an embodiment of the invention.
Figure 2:
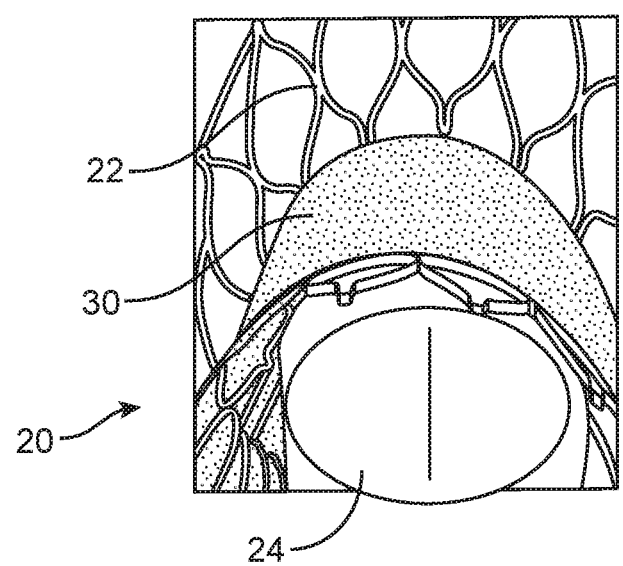
FIG. 2 is a bottom view of the paravalvular leakage resistant prosthetic heart valve of FIG. 1b.

The valve structure 24 is drawn generally in FIG. 1a and the valve structure 24 is omitted from FIG. 1b to enhance understanding of the other aspects of the invention because as referred to herein, the prosthetic heart valve 20 as used in accordance with the various devices and methods may include a wide variety of different configurations, such as a bioprosthetic heart valve structure having one or more tissue leaflets or a synthetic heart valve structure having one or more polymeric, metallic, or tissue-engineered leaflets, and can be specifically configured for replacing any heart valve.

In accordance with embodiments hereof, one or more portions of the valve structure, body, component, or member, and valve leaflets thereof, can be formed, for example, from one or more biocompatible synthetic materials, synthetic polymers, autograft tissue, homograft tissue, xenograft tissue, or one or more other suitable materials. In some embodiments, one or more portions of the valve structure and valve leaflets thereof can be formed, for example, from bovine, porcine, equine, ovine, and/or other suitable animal tissues. In accordance with embodiments hereof, one or more portions of the valve structure and valve leaflets thereof may be made of or formed from a natural material obtained from, for example, heart valves, aortic roots, aortic walls, aortic leaflets, pericardial tissue, such as pericardial patches, bypass grafts, blood vessels, intestinal submucosal tissue, umbilical tissue and the like from humans or animals. In accordance with other embodiments hereof, synthetic materials suitable for use as valve structure components and valve leaflets thereof include DACRON® polyester commercially available from Invista North America S.A.R.L. of Wilmington, Del., other cloth materials, nylon blends, polymeric materials, and vacuum deposition nitinol fabricated materials. In an embodiment, one or more portions of the valve structure and valve leaflets thereof can be made of an ultra-high molecular weight polyethylene material commercially available under the trade designation DYNEEMA from Royal DSM of the Netherlands. With certain leaflet materials, it may be desirable to coat one or both sides of the leaflet with a material that will prevent or minimize overgrowth. It is further desirable that the leaflet material is durable and not subject to stretching, deforming, or fatigue. In accordance with other embodiments hereof, the valve structure can comprise one or more valve leaflets. For example, the valve structure can be in the form of a tri-leaflet valve, a bi-leaflet valve, a quad-leaflet valve or another suitable valve. In accordance with other embodiments hereof, the valve structure can comprise two or three leaflets that are fastened together at enlarged lateral end regions to form commissural joints, with the unattached edges forming coaptation edges of the valve structure. In accordance with other embodiments hereof, the prosthetic valve leaflets can be fastened to a skirt of a graft material, which in turn can be attached or coupled to the stent frame.

As referred to herein, the prosthetic heart valve 20 as used in accordance with the devices and methods of the present disclosure can be generally used for replacement of a native aortic, mitral, pulmonic or tricuspid valve. The prosthetic heart valve 20 can also be used as a venous valve, or to replace a failed bioprosthesis, such as in the area of an aortic, mitral, pulmonic or tricuspid valve.

Figure 5:
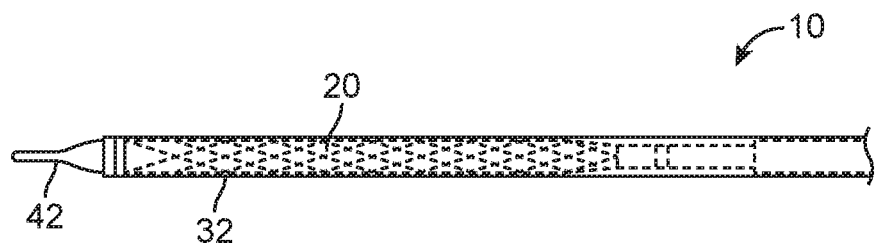
FIG. 5 is a side view of the paravalvular leakage resistant prosthetic heart valve in a loaded configuration associated with a delivery system.

The stent frame 22 is positionable in an expanded arrangement (FIGS. 1a and 1b) for maintaining the prosthetic heart valve 20 in a desired location such as with respect to the native valve. The stent is positionable in a collapsed configuration for loading within the delivery system as illustrated in FIG. 5.

FIG. 1a is a front or side view of a prosthetic heart valve 20 in accordance with an embodiment hereof. The prosthetic heart valve 20 includes a valve structure 24 supported within a stent frame 22. Stent frame 22 may include an inlet portion 25, an hourglass-shaped central or valve-retaining tubular portion 26, an outlet portion 27, support arms 28, and a sealing mechanism 30. Support arms 28 may be configured to capture leaflets during delivery of the prosthetic heart valve 20. Central portion 26 may be configured to pinch a muscular ridge of the native annulus when implanted therein. The reduced-waist region of the hourglass shape or profile of stent frame 22 may be located on or defined within central portion 26 around the entire circumference of stent frame 22. Stent frame 22 may also provide axial fixation by creating tensioning of the chordae tendinae. Sealing mechanism 30 may be positioned over at least a portion of the outer surface of stent frame 22.

FIG. 1b is a front or side view of a prosthetic heart valve 20 in accordance with an embodiment hereof. The prosthetic heart valve 20 includes a valve structure supported within a stent frame 22 and a sealing mechanism 30 positioned over at least a portion of the outer surface of stent frame 22.

In certain embodiments, the stent frame 22 is constructed to self-deploy or self-expand when released from the delivery system. For example, the stented prosthetic heart valve useful with the present disclosure can be a prosthetic valve sold under the trade name CoreValve® available from Medtronic, Inc. Other non-limiting examples of transcatheter heart valve prostheses useful with systems and methods of the present disclosure are described in U.S. Pat. No. 8,052,750; U.S. Patent Publication Nos. 2006/0265056; 2007/0239266; and 2007/0239269, and U.S. patent application Ser. No. 14/175,100, the teachings of each of which are incorporated herein by reference.

Some embodiments of the stent frames 22 can be a series of wires, wire segments and/or struts arranged such that they are capable of self-transitioning from a collapsed arrangement to a radially expanded arrangement. In constructions, one or more portions of the stent frame support structure 22 can be formed of one or more metals and/or other materials.

The wires and/or struts may be arranged in such a way that the stent frame support structure allows for folding or compressing or crimping to a compressed or compacted arrangement in which its internal diameter is smaller than its internal diameter when in the expanded arrangement. In some embodiments, the valve prosthesis comprising a stent frame support structure with an attached or coupled valve structure can be mounted in a collapsed or compressed configuration or arrangement into or onto a delivery system.

In some embodiments, the stent frame 22 can be capable of self-transitioning from the collapsed configuration to the radially expanded configuration. The material from which the stent frame 22 is fabricated can permit the stent frame 22 to be compressed and re-expanded multiple times without damaging the structure of the stent frame 22.

The wires of the stent frame support structure 22 in embodiments of the present disclosure can be formed from a shape memory material such as a nickel titanium alloy (e.g., Nitinol™). With this material, the stent frame support structure 22 is self-expandable from the compressed arrangement to the expanded arrangement, such as by the removal of external forces (e.g., compressive forces) or by the application of heat, energy, and the like.

As an alternative to fabricating the stent frame 22 from a plurality of wires, the stent frame 22 may be laser-cut from a single piece of material. In other embodiments, the valve structure 24 and the stent frame 22 can be fabricated at the same time, such as may be accomplished using high-strength nano-manufactured NiTi films produced at Advance BioProsthetic Surfaces (ABPS).

To transform between a compressed arrangement and a deployed arrangement, the stent frame support structure in accordance with embodiments described herein may be formed from a self-expanding material that has a mechanical memory to return to the deployed configuration. Accordingly in accordance with embodiments hereof, stent frames may be made from stainless steel, a pseudo-elastic metal such as a nickel titanium alloy or nitinol, or a so-called super alloy, which may have a base metal of nickel, cobalt, chromium, or other metal. Mechanical memory may be imparted to a tubular structure that may form stent frames by thermal treatment to achieve a spring temper in stainless steel, for example, or to set a shape memory in a susceptible metal alloy, such as nitinol, or a polymer, such as any of the polymers disclosed in U.S. Patent Publication No. 2004/0111111, which is incorporated by reference herein in its entirety. In accordance with other embodiments hereof, a stent frame of the valve prosthesis can be formed entirely or in part by a biocompatible or biodegradable material. In accordance with other embodiments hereof, one or more portions of a stent frame of the valve prosthesis may be self-expandable, balloon expandable, and/or mechanically-expandable.

One or more valve prosthesis embodiments disclosed herein may comprise a single support arm, a plurality of support arms, support arms with inner and outer support arm members, variations of structures thereof, and/or one more pairs of support arms having various structures and attachment points for providing various functions when implanted. It should be understood that the illustrated embodiments hereof are not limited to the number or configuration of support arms illustrated in each figure and that one or more support arms, one or more pairs of support arms and/or the various structures therefore may be substituted across the various embodiments disclosed herein without departing from the scope hereof.

In one or more embodiments, valve prosthesis may comprise one or more support arms for engaging one or more native valve leaflets. In one or more embodiments, valve prosthesis may comprise one or more support arms for engaging one or more native chordae. In one or more embodiments, valve prosthesis may comprise one or more support arms for engaging one or more native valve commissures. In one or more embodiments, valve prosthesis may comprise one or more support arms for engaging a native valve annulus. In one or more embodiments, valve prosthesis may comprise one or more support arms for engaging one or more native valve tissues or structures. For example, one or more support arms may engage or interact with valve leaflets, chordae, commissures and/or annulus. In one or more embodiments, valve prosthesis may comprise one or more support arms for engaging one or more heart tissues or structures. In one or more embodiments, valve prosthesis may comprise one or more support arms for engaging the pulmonary artery. In one or more embodiments, valve prosthesis may comprise one or more support arms for engaging the aorta.

In one or more embodiments, one or more support arms may be coupled or connected to a central portion, an inflow portion and/or an outflow portion of valve prosthesis. In one or more embodiments, valve prosthesis may comprise one or more support arms that may apply one or more forces such as a radial force, an axial force, a lateral force, an inward force, an outward force, an upstream force, and/or a downstream force to one or more valve structures, valve tissues, heart structures and/or heart tissues. In some embodiments, one or more support arms, as described herein, may be considerably longer, shorter, wider, or narrower than shown. In some embodiments, one or more support arms, as described herein, may be narrower at the base, bottom or proximal end portion where the support arms couple to the inflow portion, central portion and/or the outflow portion of the valve prosthesis and wider at the top or distal end portion of the support arm. In some embodiments, one or more support arms, as described herein, may be wider at the base, bottom, or proximal end portion where the support arms couple to the inflow portion, central portion and/or the outflow portion of the valve prosthesis and narrower at the top or distal end portion of the support arm. In some embodiments, one or more support arms, as described herein, may be configured to be a shape and size that can provide a positioning function, valve leaflet capturing function, a stabilization function, an anti-migration function, and/or an anchoring function for valve prosthesis in accordance herewith when the prosthesis is deployed at a native valve site. In some embodiments, one or more support arms, as described herein, may interact, engage, capture, clamp, push against one or more native tissues or structures such as valve leaflets, chordae, annulus, ventricle, and/or atrium. In some embodiments, one or more support arms, as described herein, may comprise a first portion that extends in a forward direction and a second portion that extends in a backward direction. In some embodiments, one or more support arms, as described herein, may comprise a first portion that extends in a backward direction and a second portion that extends in a forward direction. In some embodiments, one or more support arms, as described herein, may comprise one or more portions that may extend horizontally, longitudinally, axially, circumferentially, inward, outward, forward, and/or backward. In some embodiments, one or more support arms, as described herein, may comprise more than one configuration. For example, one or more embodiments of one or more support arms, as described herein, may extend in first direction in a delivery, compressed, and/or collapsed configuration and in a second direction in a deployed or expanded configuration. In one example, a first or delivery direction may be a forward direction and a second or deployed direction may be a backward direction. In another example, a first or delivery direction may be a backward direction and a second or deployed direction may be a forward direction. In one or more embodiments, one or more support arms, as described herein, may comprise a first shape in a delivery configuration and a second shape in a deployed configuration. For example, a first or delivery shape may be a straight shape and a second or deployed shape may be a curved shape.

In some embodiments, one or more support arms, as described herein, may comprise one or more portions that comprise one or more spiral shapes, S-shapes, C-shapes, U-shapes, V-shapes, loop shapes, tine shapes, and/or prong shapes. In some embodiments, one or more support arms, as described herein, may comprise a curved, rounded, and/or flared distal end portion. In some embodiments, one or more support arms, as described herein, may be connected, coupled, attached, and/or extend from one or more locations positioned on the inflow portion, the central portion and/or the outflow portion of the valve prosthesis. For example, in some embodiments, one or more support arms, as described herein, may be connected, coupled, attached, and/or extend from one or more locations positioned on the inflow portion, the central portion and/or the outflow portion of the valve prosthesis stent frame support structure. In some embodiments, one or more support arms, as described herein, may comprise at least a portion that may comprise at least one free end not attached or coupled to the stent frame of the valve prosthesis. In one or more embodiments, one or more support arms and/or one or more of components of a support arm may comprise one or more fixation elements or members such as anchors, barbs, prongs, clips, grommets, sutures, and/or screws. In one or more embodiments, one or more support arms and/or one or more of components of a support arm may comprise, for example, one or more active and/or passive fixation elements or members.

In one or more embodiments, valve prosthesis may comprise an inflow portion, a central portion, and an outflow portion. In one or more embodiments, the valve prosthesis may comprise a single unitary structure or the valve prosthesis may comprise one or more components or portions coupled or connected together. In one or more embodiments, the valve prosthesis may comprise a central portion comprising a valve body, member, or component. In one or more embodiments, the valve body, structure, member, or component may comprise one or more valve leaflets. In one or more embodiments in accordance herewith, the valve leaflets of the valve body, structure, member, or component are attached to an upstream end of the central portion to extend into an inflow portion of the frame, such that the valve body, structure, member, or component is not solely located on or within the outflow portion of the frame. In one or more embodiments, valve member and/or one or more of its components may comprise one or more materials, as described herein.

In one or more embodiments, the central portion of valve prosthesis and/or one or more of its components may comprise one or more longitudinal or cross-sectional shapes, such as a geometric shape, a non-geometric shape, a tubular shape, a cylindrical shape, a circular shape, an elliptical shape, an oval shape, a triangular shape, a rectangular shape, a hexagonal shape, a square shape, an hourglass shape, a polygonal shape, a funnel shape, a nozzle shape, a D-shape, a saddle shape, a planar shape, a non-planar shape, a simple geometric shape, and/or a complex geometric shape. In one or more embodiments, the central portion and/or one or more of its components may comprise one or more fixation elements or members such as anchors, barbs, clips, prongs, grommets, sutures, and/or screws. In one or more embodiments, the central portion and/or one or more of its components may comprise a frame, a framework, or stent-like structure, as described herein. In one or more embodiments, the outflow portion and/or one or more of its components may comprise, be covered with, be coated with, or be attached or coupled to one or more materials, as described herein. In one or more embodiments, the central portion and/or one or more of its components may comprise one or more support arms, components, or members as described herein. In one or more embodiments, one or more support arms may comprise one or more cantilever components or portions. In one or more embodiments, the central portion and/or one or more of its components, such as one or more support arms, may be designed to engage and/or push against the native valve annulus. In one or more embodiments, the central portion and/or one or more of its components, such as one or more support arms, may be designed to engage, capture, clamp, hold, and/or trap one or more native valve leaflets. In one or more embodiments, the central portion and/or one or more of its components, such as one or more support arms, may be designed to engage, capture, clamp, hold, and/or trap one or more native chordae. In one or more embodiments, one or more support arms may create or exert a tension force to native chordae. In one or more embodiments, the central portion and/or one or more of its components, such as one or more support arms, may be designed to engage and/or push against one or more native valve commissures.

In one or more embodiments, valve prosthesis may comprise an inflow, inlet, upstream, or proximal portion connected, coupled, positioned, and/or located at a proximal end or proximal end portion of the central portion of the valve prosthesis. In one or more embodiments, the inflow portion and/or one or more of its components may contact, engage, fixate, capture, clamp, pierce, hold, position, and/or seal the valve prosthesis to one or more heart structures and/or tissues such as atrial tissue, ventricle tissue, valve tissue, annulus tissue, the floor of an atrium, and/or the floor of a ventricle. For example, the inflow portion and/or one or more of its components may engage atrial tissue if the valve prosthesis is positioned in a native mitral valve whereas the inflow portion and/or one or more of its components may engage ventricle tissue if the valve prosthesis is positioned in a native aortic valve. In one or more embodiments, the inflow portion and/or one or more of its components may exert one or more forces, for example, radial and/or axial forces, to one or more heart structures and/or heart tissues. In one or more embodiments, the inflow portion and/or one or more of its components may comprise one or more fixation elements or members such as anchors, barbs, clips, prongs, grommets, sutures, and/or screws. In one or more embodiments, the inflow portion and/or one or more of its components may comprise one or more longitudinal or cross-sectional shapes, such as a geometric shape, a non-geometric shape, a tubular shape, a cylindrical shape, a circular shape, an elliptical shape, an oval shape, a triangular shape, a rectangular shape, a hexagonal shape, a square shape, a polygonal shape, a funnel shape, a nozzle shape, a D-shape, an S-shape, a saddle shape, a simple geometric shape, and/or a complex geometric shape. In one or more embodiments, the inflow portion and/or one or more of its components may be designed to deform to the shape of the native anatomy when the valve prosthesis is implanted. For example, the inflow portion may deform from a pre-delivery circular shape to a post-delivery D-shape following the delivery of the valve prosthesis to a native mitral valve. In one or more embodiments, the inflow portion and/or one or more of its components may comprise a frame, a framework, or stent-like structure, as described herein. In one or more embodiments, the inflow portion and/or one or more of its components may comprise, be covered with, be coated with, or be attached or coupled to one or more materials, as described herein. In one or more embodiments, the inflow portion and/or one or more of its components may comprise one or more support arms, components, or members as described herein. In one or more embodiments, one or more support arms may comprise one or more cantilever components or portions. In one or more embodiments, the inflow portion and/or one or more of its components, such as one or more support arms, may be designed to engage and/or push against the native valve annulus. In one or more embodiments, the inflow portion and/or one or more of its components, such as one or more support arms, may be designed to engage, capture, clamp, hold, and/or trap one or more native valve leaflets. In one or more embodiments, the inflow portion and/or one or more of its components, such as one or more support arms, may be designed to engage, capture, clamp, hold, and/or trap one or more native chordae. In one or more embodiments, one or more support arms may create or exert a tension force to native chordae. In one or more embodiments, the inflow portion and/or one or more of its components, such as one or more support arms, may be designed to engage and/or push against one or more native valve commissures.

In one or more embodiments, valve prosthesis may comprise an outflow, outlet, downstream, or distal portion connected, coupled, positioned, and/or located at a distal end or distal end portion of the central portion of the valve prosthesis. In one or more embodiments, the outflow portion and/or one or more of its components may contact, engage, fixate, capture, clamp, pierce, hold, position, and/or seal the valve prosthesis to one or more heart structures and/or tissues such as atrial tissue, ventricle tissue, valve tissue, valve leaflet tissue, annulus tissue, and/or chordae tissue. For example, the outflow portion and/or one or more of its components may engage leaflet tissue, chordae tissue, and/or ventricle tissue if the valve prosthesis is positioned in a native mitral valve whereas the outflow portion and/or one or more of its components may engage leaflet tissue and/or aortic tissue if the valve prosthesis is positioned in a native aortic valve. In one or more embodiments, the outflow portion and/or one or more of its components may exert one or more forces, for example, radial and/or axial forces, to one or more heart structures and/or heart tissues. In one or more embodiments, the outflow portion and/or one or more of its components may comprise one or more fixation elements or members such as anchors, barbs, prongs, clips, grommets, sutures, and/or screws. In one or more embodiments, the outflow portion and/or one or more of its components may comprise one or more longitudinal or cross-sectional shapes, such as a geometric shape, a non-geometric shape, a tubular shape, a cylindrical shape, a circular shape, an elliptical shape, an oval shape, a triangular shape, a rectangular shape, a hexagonal shape, a square shape, a polygonal shape, a funnel shape, a nozzle shape, a D-shape, an S-shape, a saddle shape, a simple geometric shape, and/or a complex geometric shape. In one or more embodiments, the outflow portion and/or one or more of its components may be designed to deform to the shape of the native anatomy when the valve prosthesis is implanted. For example, the outflow portion may deform from a pre-delivery circular shape to a post-delivery D-shape following the delivery of the valve prosthesis to a native mitral valve. In one or more embodiments, the outflow portion and/or one or more of its components may comprise a frame, a framework, or stent-like structure, as described herein. In one or more embodiments, the outflow portion and/or one or more of its components may comprise, be covered with, be coated with, or be attached or coupled to one or more materials, as described herein. In one or more embodiments, the outflow portion and/or one or more of its components may comprise one or more support arms, components, or members as described herein. In one or more embodiments, the outflow portion and/or one or more of its components, such as one or more support arms, may be designed to engage, capture, clamp, hold, and/or trap one or more native valve leaflets. In one or more embodiments, the outflow portion and/or one or more of its components, such as one or more support arms, may be designed to engage, capture, clamp, hold, and/or trap one or more native chordae. In one or more embodiments, one or more support arms may create or exert a tension force to native chordae. In one or more embodiments, the outflow portion and/or one or more of its components, such as one or more support arms, may be designed to engage and/or push against one or more native valve commissures. In one or more embodiments, the outflow portion and/or one or more of its components, such as one or more support arms, may be designed to engage and/or push against the native valve annulus. In one or more embodiments, one or more support arms may comprise one or more cantilever components or portions.

In one or more embodiments, valve prosthesis and/or one or more of its components or portions may comprise, be covered with, be coated with, or be attached or coupled to one or more biocompatible materials or biomaterials, for example, titanium, titanium alloys, Nitinol, TiNi alloys, shape memory alloys, super elastic alloys, aluminum oxide, platinum, platinum alloys, stainless steels, stainless steel alloys, MP35N, elgiloy, haynes 25, stellite, pyrolytic carbon, silver carbon, glassy carbon, polymers or plastics such as polyamides, polycarbonates, polyethers, polyesters, polyolefins including polyethylenes or polypropylenes, polystyrenes, polyurethanes, polyvinylchlorides, polyvinylpyrrolidones, silicone elastomers, fluoropolymers, polyacrylates, polyisoprenes, polytetrafluoroethylenes, polyethylene terephthalates, fabrics such as woven fabrics, nonwoven fabrics, porous fabrics, semi-porous fabrics, nonporous fabrics, Dacron fabrics, polytetrafluoroethylene (PTFE) fabrics, polyethylene terephthalate (PET) fabrics, materials that promote tissue ingrowth, rubber, minerals, ceramics, hydroxapatite, epoxies, human or animal protein or tissue such as collagen, laminin, elastin or fibrin, organic materials such as cellulose, or compressed carbon, and/or other materials such as glass, and the like. Materials that are not considered biocompatible may be modified to become biocompatible by a number of methods well known in the art. For example, coating a material with a biocompatible coating may enhance the biocompatibility of that material. Biocompatible materials or biomaterials are usually designed and constructed to be placed in or onto tissue of a patient's body or to contact fluid of a patient's body. Ideally, a biocompatible material or biomaterial will not induce undesirable reactions in the body such as blood clotting, tumor formation, allergic reaction, foreign body reaction (rejection) or inflammatory reaction; will have the physical properties such as strength, elasticity, permeability, and flexibility required to function for the intended purpose; may be purified, fabricated and sterilized easily; will substantially maintain its physical properties and function during the time that it remains in contact with tissues or fluids of the body.

In one or more embodiments, valve prosthesis and/or one or more of its components or portions may comprise and/or be coupled or attached to one or more graft materials. In accordance with embodiments hereof, the graft material or portions thereof may be a low-porosity woven fabric, such as polyester, DACRON® polyester, or polytetrafluoroethylene (PTFE), which creates a one-way fluid passage when attached to the stent frame of the valve prosthesis. In an embodiment, the graft material or portions thereof may be a looser knit or woven fabric, such as a polyester or PTFE knit, which can be utilized when it is desired to provide a medium for tissue ingrowth and the ability for the fabric to stretch to conform to a curved surface. In another embodiment, polyester velour fabrics may alternatively be used for the graft material or portions thereof, such as when it is desired to provide a medium for tissue ingrowth on one side and a smooth surface on the other side. These and other appropriate cardiovascular fabrics are commercially available from Bard Peripheral Vascular, Inc. of Tempe, Ariz., for example. In another embodiment, the graft material or portions thereof may be a natural material, such as pericardium or another membranous tissue.

In one or more embodiments, valve prosthesis and/or one or more of its components or portions may comprise, be coated with, be covered with, be constrained by, or be attached or coupled to a shape memory material, a bioresorbable material, and/or a biodegradable material, such as a natural or synthetic biodegradable polymer, non-limiting examples of which include polysaccharides such as alginate, dextran, cellulose, collagen, and chemical derivatives thereof, proteins such as albumin, and copolymer blends thereof, alone or in combination with synthetic polymers, polyhydroxy acids, such as polylactides, polyglycolides and copolymers thereof, poly(ethylene terephthalate), poly(hydroxybutyric acid); poly(hydroxyvaleric acid), poly [lactide-co-(E-caprolactone)]; poly[glycolide-co-(E-caprolactone)], polycarbonates, poly(pseudo amino acids); poly(amino acids); poly(hydroxyalkanoate)s, polyanhydrides; polyortho esters, and blends and copolymers thereof. In one or more embodiments, one or more surfaces of the valve prosthesis and/or one or more of its components or portions may comprise, be covered with, be coated with, or be attached or coupled to one or more glues and/or adhesives, such as a bioglue or bioadhesive used to help anchor and/or seal the valve prosthesis to native tissue.

In one or more embodiments, one or more surfaces of the valve prosthesis and/or one or more of its components or portions may comprise, be covered with, be coated with, or be attached or coupled to one or more radioactive materials and/or biological agents, for example, an anticoagulant agent, an antithrombotic agent, a clotting agent, a platelet agent, an anti-inflammatory agent, an antibody, an antigen, an immunoglobulin, a defense agent, an enzyme, a hormone, a growth factor, a neurotransmitter, a cytokine, a blood agent, a regulatory agent, a transport agent, a fibrous agent, a protein, a peptide, a proteoglycan, a toxin, an antibiotic agent, an antibacterial agent, an antimicrobial agent, a bacterial agent or component, hyaluronic acid, a polysaccharide, a carbohydrate, a fatty acid, a catalyst, a drug, a vitamin, a DNA segment, a RNA segment, a nucleic acid, a lectin, an antiviral agent, a viral agent or component, a genetic agent, a ligand and/or a dye (which acts as a biological ligand). Biological agents may be found in nature (naturally occurring) or may be chemically synthesized by a variety of methods well known in the art.

In one or more embodiments, valve prosthesis and/or one or more of its components or portions may comprise, be coated with, be covered with, or be attached or coupled to one or more biological cells or tissues, for example, tissue cells, cardiac cells, contractile cells, muscle cells, heart muscle cells, smooth muscle cells, skeletal muscle cells, autologous cells, allogenic cells, xenogenic cells, stem cells, genetically engineered cells, non-engineered cells, mixtures of cells, precursor cells, immunologically neutral cells, differentiated cells, undifferentiated cells, natural tissue, synthetic tissue, animal tissue, human tissue, porcine tissue, equine tissue, porcine tissue, bovine tissue, ovine tissue, autologous tissue, allogenic tissue, xenogenic tissue, autograft tissue, genetically engineered tissue, non-engineered tissue, mixtures of tissues, cardiac tissue, pericardial tissue, cardiac valve tissue, membranous tissue, and/or intestinal submucosa tissue. In one or more embodiments, valve prosthesis and/or one or more of its components or portions may comprise, be covered with, be coated with, or be attached or coupled to one or more materials that promote the growth of cells and/or tissue. In one or more embodiments, the cell and/or tissue promoting materials may comprise, possess or be configured to possess physical characteristics such as size, shape, porosity, matrix structure, fiber structure, and/or chemical characteristics such as growth factors, biological agents, that promote and/or aid, for example, in the adherence, proliferation and/or growth of desired cells and/or tissues in vivo following implantation or ex vivo prior to implantation. In one or more embodiments, the cell and/or tissue promoting materials may accelerate the healing response of the patient following the implantation of the valve prosthesis. In one or more embodiments, the cell and/or tissue promoting materials may comprise pockets, parachutes, voids, and/or openings, for example, that may trap cells and/or tissues and/or promote cells and/or tissues to proliferate, grow and/or heal.

In one or more embodiments, the valve prosthesis may comprise one or more active and/or passive fixation elements or members such as anchors, barbs, prongs, clips, grommets, sutures, and/or screws. In one or more embodiments, one or more active and/or passive fixation elements or members may be delivered separately from the valve prosthesis. In one or more embodiments, one or more active and/or passive fixation elements or members may be delivered during the valve prosthesis implant procedure. In one or more embodiments, one or more active and/or passive fixation elements or members may be delivered after the valve prosthesis implant procedure. In one or more embodiments, one or more active and/or passive fixation elements or members may be delivered using the valve prosthesis delivery system. In one or more embodiments, one or more active fixation elements or members may be activated by pushing, pulling, twisting, screwing and/or turning motion or movement. In one or more embodiments, one or more fixation elements or members may be released or engaged via an unsheathing, an unsleeving, a dissolving, and/or a degrading action. In one or more embodiments, one or more active and/or passive fixation elements or members may be delivered using a fixation element delivery system. In one or more embodiments, one or more active and/or passive fixation elements or members may be coupled, connected, and/or attached to the valve prosthesis stent or frame. In one or more embodiments, the valve prosthesis stent or frame may comprise a unitary structure that comprises one or more active and/or passive fixation elements. In one or more embodiments, one or more active and/or passive fixation elements may be coupled, connected, and/or attached to the valve prosthesis skirt and/or graft material. In one or more embodiments, one or more fixation elements or members may be designed to increasingly engage one or more heart tissues and/or structures via any movement of the valve prosthesis relative to heart tissue and/or structures during one or more cardiac cycles. For example, a barbed fixation element that further embeds itself into tissue via movement of the valve prosthesis relative to tissue in one direction and then resists movement of the valve prosthesis relative to tissue in the opposite direction.

In one or more embodiments, the valve prosthesis 20 may comprise one or more posts or tabs 29 circumferentially spaced about a circumference defined by the stent frame 22. The posts or tabs 29 can assume various forms, and in some embodiments are identical. One or more posts or tabs 29 may comprise one or more slots or openings. The posts or tabs 29 can be used to couple or retain the valve prosthesis 20 to a valve deployment or delivery system 10.

In certain embodiments, the valve prosthesis 20 is configured for repairing an aortic valve. Alternatively, other shapes are also envisioned to adapt to the specific anatomy of the valve to be repaired (e.g., stented prosthetic heart valves in accordance with the present disclosure can be shaped and/or sized for replacing a native aortic, mitral, pulmonic and/or tricuspid valve).

The prosthetic heart valve 20 described herein may be implanted into an annulus of a native cardiac valve via a suitable delivery route or procedure. For example, the valve prosthesis 20 may be delivered through an artery or vein, a femoral artery, a femoral vein, a jugular vein, a subclavian artery, an axillary artery, an aorta, an atrium, and/or a ventricle. The valve prosthesis 20 may be delivered via a transfemoral, transapical, transseptal, transatrial, transventrical, or transaortic procedure.

In some embodiments, an aortic valve prosthesis 20 may be delivered transfemorally. In such a delivery, a delivery device 10 and the valve prosthesis 20 can be advanced in a retrograde manner through the femoral artery and into the patient's descending aorta. The delivery device 10 and valve prosthesis 20 can then be advanced under fluoroscopic guidance over the aortic arch, through the ascending aorta, and mid-way across the defective aortic valve. Once positioning of the catheter is confirmed, the delivery device 10 can deploy the valve prosthesis 20 within the defective valve in a stepped deployment procedure. The valve prosthesis 20 can then expand against and align the prosthesis within the defective valve.

In some embodiments, a mitral valve prosthesis 20 may be delivered transfemorally. In such a delivery, a delivery device 10 and the valve prosthesis 20 can be advanced in a retrograde manner through the femoral artery and into the patient's descending aorta. The delivery device 10 and valve prosthesis 20 can then be advanced under fluoroscopic guidance over the aortic arch, through the ascending aorta, into the left ventricle, and mid-way across the defective mitral valve. Once positioning of the catheter is confirmed, the delivery device 10 can deploy the valve prosthesis 20 within the defective valve in a stepped deployment procedure. The valve prosthesis 20 can then expand against and align the prosthesis within the defective valve.

In some embodiments, a valve prosthesis 20 can be delivered via a transapical procedure. In a transapical procedure, a delivery device 10 and the valve prosthesis 20 can be inserted into a patient's left ventricle through an incision created in the apex of the patient's heart. A dilator may be used to aid in the insertion of the delivery device 10 and the valve prosthesis 20. In this approach, the native valve (for example, a mitral valve or an aortic valve) may be approached from either a downstream direction relative to the blood flow for a mitral valve or an upstream direction relative to the blood flow for an aortic valve. The delivery device 10 and valve prosthesis 20 may be advanced mid-way across the defective valve. Once positioning of the catheter is confirmed, the delivery device 10 can deploy the valve prosthesis 20 within the defective valve in a stepped deployment procedure. The valve prosthesis 20 can then expand against and align the prosthesis within the defective valve.

In some embodiments, a mitral valve prosthesis 20 can be delivered via a transatrial procedure. In such a procedure, a delivery device 10 and the valve prosthesis 20 can be inserted through an incision made in the wall of the left atrium of the patient's heart. The delivery device 10 and valve prosthesis 20 may be advanced mid-way across the defective mitral valve. Once positioning of the catheter is confirmed, the delivery device 10 can deploy the valve prosthesis 20 within the defective valve in a stepped deployment procedure. The valve prosthesis 20 can then expand against and align the prosthesis within the defective valve.

In some embodiments, an aortic valve prosthesis 20 can be delivered via a transatrial procedure. In such a procedure, a delivery device 10 and the valve prosthesis 20 can be inserted through an incision made in the wall of the left atrium of the patient's heart. The delivery device 10 and the valve prosthesis 20 may be advanced through the left atrium, through the mitral valve, into the left ventricle, and mid-way across the defective aortic valve. Once positioning of the catheter is confirmed, the delivery device 10 can deploy the valve prosthesis 20 within the defective valve in a stepped deployment procedure. The valve prosthesis 20 can then expand against and align the prosthesis within the defective valve.

In one or more embodiments of the present invention, valve prosthesis 20 and/or one or more of its components or portions may be delivered, for example, through a thoracotomy, a sternotomy, percutaneously, transvenously, arthroscopically, endoscopically, for example, through a percutaneous port, a stab wound or puncture, through a small incision, for example, in the chest, groin, abdomen, neck, leg, arm, or in combinations thereof. In one or more embodiments of the present invention, valve prosthesis 20 and/or one or more of its components or portions may be delivered, for example, via a transvascular method, a transarterial method, a transvenous method, a transcardiac method, a transatrial method, a transventrical method, transapical method, a transseptal method, a transaortic method, a transcatheter method, a surgical method, a beating heart method, a stopped heart method, a pump-assisted method, and/or a cardiopulmonary bypass method.

In one or more embodiments of the present invention, valve prosthesis 20 and/or one or more of its components or portions may be positioned in, positioned through, and/or positioned adjacent to, for example, a natural valve, a native valve, a synthetic valve, a replacement valve, a tissue valve, a mechanical valve, a mitral valve, an aortic valve, a pulmonary valve, a tricuspid valve, a valve component, a valve annulus, a valve leaflet, chordea, and/or a valve commissure.

The sealing mechanism 30 is positioned over at least a portion of the outer surface of the stent frame 22 of the prosthetic heart valve 20. In some embodiments, the sealing mechanism 30 on the prosthetic heart valve 20 may be referred to as a skirt. In other embodiments, the sealing mechanism 30 extends over a portion of an inner surface of the stent frame 22 of the prosthetic heart valve 20.

Figure 3:
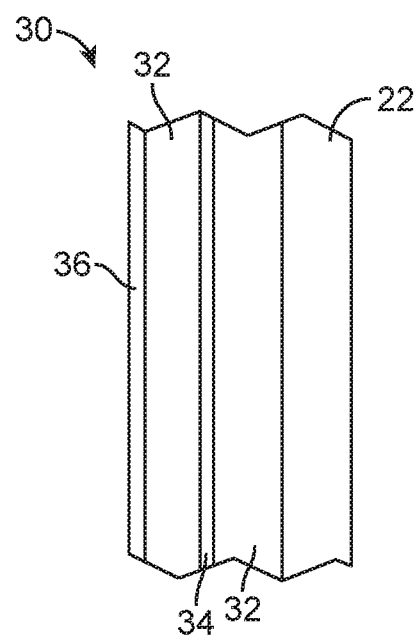
FIG. 3 is a sectional view of the paravalvular leakage resistant prosthetic heart valve.

At least a portion of the sealing mechanism 30 is fabricated from a semi-permeable membrane 32 that is used in conjunction with an osmotic gradient driving material 34, as illustrated in FIG. 3. The sealing mechanism 30 may be fabricated from multiple semi-membrane layers 32 as is discussed in more detail herein.

The semi-permeable membrane 32 used in conjunction with the sealing mechanism 30 may be fabricated from a variety of materials. One type of semi-permeable membrane 32 that is suitable for use in conjunction with the sealing mechanism 30 is a cellulosic membrane.

The cellulose membrane can be fabricated from natural materials, synthetic materials or a combination of natural materials and synthetic materials. In certain embodiments, at least one of an inner surface and an outer surface of the cellulose membrane can be modified. Examples of two suitable cellulosic membranes are cellulose ester or regenerated cellulose.

The semi-permeable membrane 32 can be formed with a pore size and selectivity based upon the osmotic gradient driving material that is used. In certain embodiments, the molecular cutoff range of the semi-permeable membrane 32 is between about 1 and 1,000,000 kilodaltons.

One or more portions of the semi-permeable membrane 32 may be coated with one or more materials as previously described. In certain embodiments, one or more portions of the semi-permeable membrane 32 may be coated with at least one protein and/or at least one biodegradable polymer coating layer 36. In certain embodiments, the coating layer 36 may prevent or substantially reduce diffusion of fluid through one or more portions of the semi-permeable membrane 32 when the prosthetic heart valve 20 is stored in a fluid solution such as an aqueous solution prior to use.

In certain embodiments, the coating layer 36 may be dissolvable upon exposure to a blood environment. For example, the coating layer 36 may rapidly dissolve and/or disintegrate upon introduction into a blood environment. The dissolvable nature of the coating layer 36 permits diffusion of fluid through the semi-permeable membrane 32 once the prosthetic heart valve 20 is in the blood environment to thereby facilitate swelling of the sealing mechanism 30.

In another embodiment, the semi-permeable membrane 32 may be coated with a coating layer 36 that is soluble in a solvent so that the coating layer 36 will dissolve and/or disintegrate upon contact with the particular solvent such as alcohol. When the prosthetic heart valve 20 is stored in an aqueous solution prior to use, the coating layer 36 restricts or prevents diffusion of fluid through the semi-permeable membrane 32 and thus prevents the swelling of the sealing mechanism 30.

In certain embodiments, prior to loading the prosthetic heart valve 20 onto the delivery system, the prosthetic heart valve 20 is briefly exposed to a solvent such as by submersion in the solvent. This exposure in a solvent causes the coating layer 36 to dissolve. Thereafter, the prosthetic heart valve 20 is implanted and the osmotic gradient driving material 34 promotes diffusion of fluid through the semi-permeable membrane 32 to thereby cause osmotic swelling of the sealing mechanism 30.

The osmotic gradient driving material 34 is associated with the sealing mechanism 30. In certain embodiments, the osmotic gradient driving material is placed in an interior of the sealing mechanism 30. For example, the osmotic gradient driving material 34 may be placed between semi-permeable membrane layers 32 used in fabricating the sealing mechanism 30. In another embodiment, the osmotic gradient driving material 34 is incorporated in one or more materials that are used to fabricate sealing mechanism 30 such as one or more portions of the semi-permeable membrane 32.

A variety of materials may be utilized to drive an osmotic gradient in the sealing mechanism 30. In certain embodiments, the osmotic gradient driving materials are organic and/or inorganic compounds that are either positively or negatively charged. Examples of suitable organic compounds include polysaccharides such as glycosaminoglycans. The organic compounds can also be proteins. Examples of suitable proteins include natural or synthetic peptides containing charged amino acid residues.

Examples of suitable inorganic compounds include synthetic particles such as polyionic microbeads or nanoparticles. Other suitable inorganic compounds include sodium chloride or other salts that are conventionally found in physiological blood. In still other embodiments, gradient driving material 34 may comprise a combination of at least one inorganic compound such as a salt and at least one organic compound such as a charged organic compound.

The osmotic gradient driving material 34 is provided at an effective concentration. As used herein, the term effective concentration means that the osmotic gradient driving material causes a sufficient amount of fluid such as water to be drawn into the sealing mechanism 30 to provide a desired amount of swelling of the sealing mechanism 30.

The effective concentration thereby varies depending on the osmotic gradient driving material that is used in conjunction with the sealing mechanism 30. Even though a precise concentration range for the osmotic gradient driving material is not provided, it is within the expertise of a person of skill in the art to determine the suitable concentration range for a particular osmotic gradient driving material. The material used in fabricating the semi-permeable membrane 32 may also affect the swelling of the sealing mechanism 30. Such a determination would not involve undue experimentation.

The semi-permeable membrane 32 in the sealing mechanism 30 may take a variety of forms. In one configuration, there are two semi-permeable membrane layers 32 and an interstitial space therebetween. In another configuration, there are three semi-permeable membrane layers 32 with two interstitial spaces therebetween.

In certain embodiments, different materials may be placed in the two interstitial spaces. An advantage of this configuration is that it allows for swelling in the inner space as well as protein/drug diffusion from the outer semi-permeable membrane. In yet another configuration, there are greater than three semi-permeable membrane layers 32.

The osmotic gradient driving material 34 is placed in at least one of the interstitial spaces. The form of the materials that are used in the osmotic gradient driving material would impact the manner in which the osmotic gradient driving material is placed in the interstitial space.

For example, if the osmotic gradient driving material 34 is provided in a particulate form, the osmotic gradient driving material 34 may be sprinkled on one of the semi-permeable membranes 32 as an initial step in forming the sealing mechanism 30.

In other embodiments, the osmotic gradient driving material 34 may be formed into a layer that is placed between semi-permeable membrane layers 32 during the process of fabricating the sealing mechanism 30.

One or more thicknesses of one or more portions of the sealing mechanism 30 may be selected based upon a variety of factors. An example of one such factor is the irregularity of the native valve where it is desired to implant the prosthetic heart valve 20. Another factor in selecting the thickness of the sealing mechanism 30 is the inner diameter of the delivery system 10 in which the prosthetic heart valve 20 and associated sealing mechanism 30 must be compressed prior to deployment.

A factor in the thickness of the sealing mechanism 30 is the compressibility of the semi-permeable membrane 32. Additionally, forming the sealing mechanism 30 too thin may also negatively impact the strength of the sealing mechanism 30 and thereby increase the potential that the sealing mechanism 30 is damaged during the process of delivering the prosthetic heart valve 20.

In certain embodiments, the sealing mechanism 30 has a thickness of up to about 0.1 millimeters. In other embodiments, the sealing mechanism 30 has a thickness of between about 50 and 200 microns. In membrane configurations that utilize two layers, the double membrane thickness could be between about 100 and 300 microns with the additional thickness to accommodate one or more osmotic gradient driving materials such as one or more salts used in the sealing mechanism 30.

Imaging analysis of current prosthetic heart valve devices has shown gaps of up to about 5 millimeters between an outer surface of the stent frame and an inner lining of an aortic root. Because of the shape of the aortic root, this gap may not be consistent around the stent frame 22 but this gap may be particularly evident in regions of native commissure.

Therefore, the sealing mechanism 30 should be constructed to allow radial expansion or swelling of up to about 5 millimeters when placed in a blood environment as well as to permit passive diffusion of fluid such as plasma through the semi-permeable membrane 32 structure.

The sealing mechanism 30 should be formed with a swelling size that is sufficiently large so that the swelling of the sealing mechanism 30 upon exposure to blood is sufficiently large to fill any gaps between the prosthetic heart valve 20 and the native tissue. On the other hand, the swelling should not be too great as to put undue pressure on the native tissue and/or prosthetic heart valve 20 to cause collapse of the stent frame 22 and/or prevent full expansion of the stent frame 22 because such actions could impede the operation of the valve structure 24.

The sealing mechanism 30 may be fabricated with different dimensions. For example, increasing the width may provide the sealing mechanism 30 with an enhanced ability to form a seal between the prosthetic heart valve 20 and the native tissue. However, increasing the width of the sealing mechanism 30 may decrease flexibility of the sealing mechanism 30 such as when the prosthetic heart valve 20 is being delivered to the location where it is intended to be deployed.

In certain embodiments, the sealing mechanism 30 may be attached to the stent frame 22 to restrict movement of the sealing mechanism 30 with respect to the stent frame 22. A variety of techniques may be used to attach the sealing mechanism 30 to the stent frame 22. Attachment of the sealing mechanism 30 to the stent frame 22 is particularly important when the stent frame 22 is in the collapsed configuration as well as when the stent frame 22 is moving between the collapsed and expanded configurations.

In certain embodiments, one or more mechanical fasteners such as at least one suture may be used to secure the sealing mechanism 30 in a desired position with respect to the stent frame 22. The number of sutures utilized depends on factors such as the width of the sealing mechanism 30.

Another technique that can be used to attach the sealing mechanism 30 to the stent frame 22 is the use of one or more adhesives. A person of skill in the art would appreciate that there are a variety of biocompatible adhesives. One or more biocompatible adhesives may be used alone or in conjunction with one or more mechanical fasteners. Yet another technique that can be used to attach the sealing mechanism 30 to the stent frame 22 is melting and/or welding such as with direct heat or ultrasound.

Figure 4:
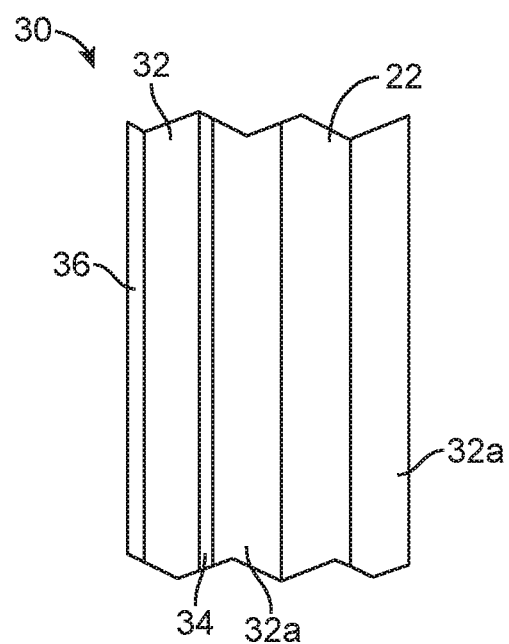
FIG. 4 is a sectional view of an alternative embodiment of the paravalvular leakage resistant prosthetic heart valve.

Another configuration for attaching the sealing mechanism 30 to the stent frame 22 involves placing layers 32a over at least a portion of the inner and outer surfaces of the stent frame 22 and then sealing these layers 32a together to thereby retain the stent frame 22 between the layers 32a, as illustrated in FIG. 4. In certain embodiments, the layers 32a are placed on opposite surfaces of the stent frame 22. In certain embodiments, one or more layers 32a may be fabricated from one or more semi-permeable membranes. In certain embodiments, at least one additional semi-permeable membrane layer 32 is attached to the layer 32a on the outer surface of the stent frame 22. In certain embodiments, an osmotic gradient material 34 is placed between the semi-permeable layer 32 and the outer layer 32a. In certain embodiments, semi-permeable membrane 32 may comprise a coating layer 36.

In certain embodiments, the sealing mechanism 30 may have a generally flat configuration and is wrapped around the outer surface of the prosthetic heart valve 20. Depending upon factors such as the thickness of the sealing mechanism 30, the sealing mechanism 30 may be wrapped around the outer surface of the prosthetic heart valve 20 more than one time.

In another embodiment, the sealing mechanism 30 may have a tubular configuration. When the sealing mechanism 30 has a tubular configuration, the sealing mechanism 30 is positioned over a portion of the outer surface of the prosthetic heart valve 20. The stent frame 22 may be moved to the collapsed configuration to facilitate placing the tubular sealing mechanism 30 thereon.

In one or more embodiments, the valve prosthesis 20 may be delivered via a delivery system 10 that comprises a catheter with a retractable compression sleeve, sheath, or capsule 32 that covers the valve prosthesis 20, as illustrated in FIG. 5, until it is to be deployed, at which point the sheath 32 may be retracted to allow the stent frame 22 to self-expand.

Figure 6:
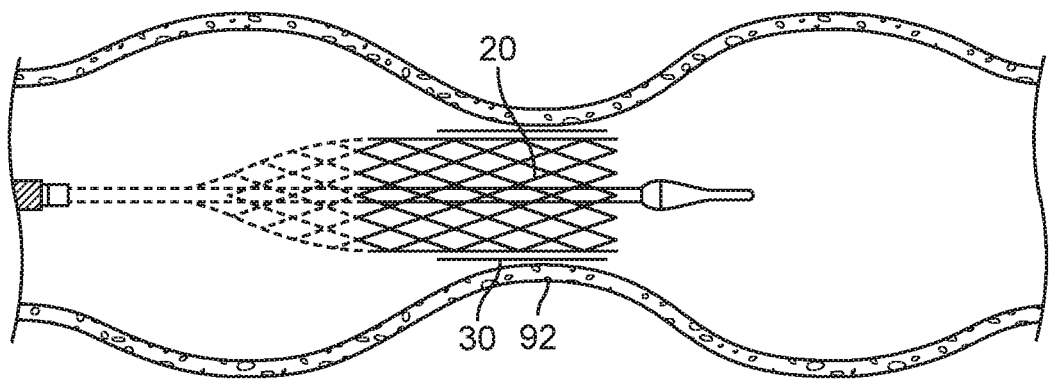
FIG. 6 is a side view of the paravalvular leakage resistant prosthetic heart valve in an expanded configuration with respect to a native annulus.

Once the prosthetic heart valve 20 is in a desired implant position, sheath 32 is retracted and the prosthetic heart valve 20 is allowed to uncompress or expand, as illustrated in FIG. 6. After implantation, a difference in salt concentration between the sealing mechanism 30 and the blood environment adjacent thereto will produce an osmotic imbalance and such osmotic imbalance will cause water in the blood to be drawn into the sealing mechanism 30. As the water is drawn into the sealing mechanism 30, the sealing mechanism 30 swells, which enhances the contact between the prosthetic heart valve 20 and the native valve, which reduces the potential of paravalvular leakage.

Force caused by swelling of the sealing mechanism 30 should be primarily directed outwards from the prosthetic heart valve 20 as inward force caused by the swelling of the sealing mechanism 30 could produce negative effects on the operation of the valve structure 24 such as impeding movement of the valve structure 24 between open and closed configurations.

For example, the swelling of the sealing mechanism 30 should not be sufficiently great so that the sealing mechanism 30 causes the stent frame 22 to collapse or otherwise deform in a manner that reduces the engagement between the prosthetic heart valve 20 and the native valve.

Additionally, the swelling of the sealing mechanism 30 should not cause migration of the prosthetic heart valve 20 with respect to the native valve. Both of the preceding phenomena could impact the success of the procedure that is performed using the prosthetic heart valve 20 according to this invention.

A variety of tests can be used to detect valve migration and/or valve frame deformation. Examples of these tests include a hydrodynamics test (pulse duplicator), which detects significant deformation of the prosthetic heart valve due to swelling of the semi-permeable membrane. A migration test can be used to detect prosthetic heart valve migration with respect to native tissue such as the aortic root. A radiopaque leakage test can be used to detect the presence of paravalvular leakage.

In operation, in one embodiment of utilizing the prosthetic heart valve deployment system 10, the components are loaded into a compressed arrangement illustrated in FIG. 5. The sealing mechanism 30 does not need to be in a stationary position with respect to the stent frame 22. In an alternative embodiment, the sealing mechanism 30 can be separate from the stent frame 22 such as distal to the stent frame 22. The sealing mechanism 30 may be pulled over the stent frame 22 during deployment such as using sutures or alternative mulling mechanisms.

A compression sleeve, sheath, or capsule 32 at least partially covers the valve prosthesis 20 and thereby secures the valve prosthesis 20 to the valve deployment system 10. In one embodiment, after appropriate preparation of the patient, the distal end of the prosthetic heart valve deployment system 10 is advanced through the patient's vascular system and advanced across a native valve 92 such as the native aortic valve.

In one embodiment, the capsule 32 is maintained in a substantially stationary position as the prosthetic heart valve 20 is advanced distally into the left ventricle. In another embodiment, the capsule 32 and the prosthetic heart valve 20 are advanced into the left ventricle. The prosthetic heart valve 20 is maintained in a substantially stationary position as the capsule 32 is proximally retracted.

Figure 7:
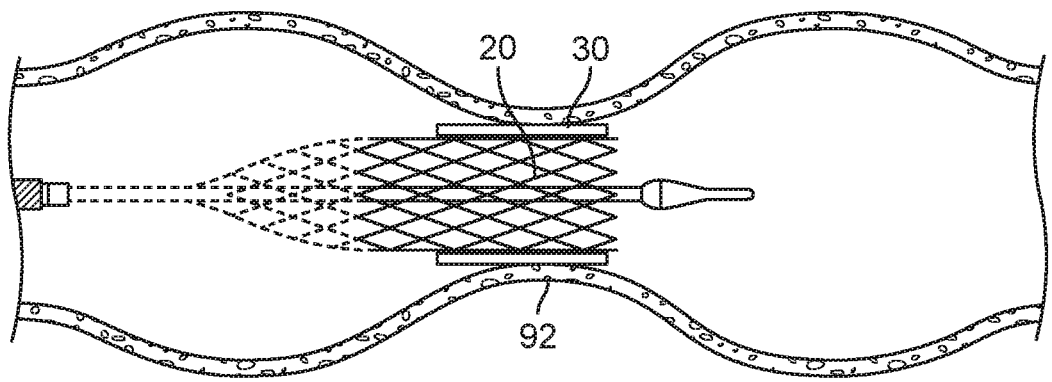
FIG. 7 is a side view of the paravalvular leakage resistant prosthetic heart valve with the sealing mechanism in a swollen configuration to enhance a seal between the prosthetic heart valve and the native annulus.

In both of the preceding configurations, the prosthetic heart valve 20 expands from the compressed arrangement to the expanded arrangement as the capsule 32 moves off the prosthetic heart valve 20, as illustrated in FIG. 6. The prosthetic heart valve 20 is then released from the deployment system, as illustrated in FIG. 7, and the deployment system 10 is removed from the patient to complete the procedure.

Movement of the capsule 32 off of the prosthetic heart valve 20 also causes the sealing mechanism 30 to come into contact with blood flowing through the cardiovascular system in which the prosthetic heart valve 20 has been implanted. The osmotic gradient driving material 34 causes fluid such as water to be drawn through the semi-permeable membrane 32, which causes the sealing mechanism 30 to swell. As illustrated in FIG. 7, such swelling of the sealing mechanism 30 enhances a seal between the prosthetic heart valve 20 and the native valve 92, which reduces the potential of blood leaking between the prosthetic heart valve 20 and the native valve 92.

While the concepts disclosed herein are described for use in conjunction with prosthetic heart valves, it is possible for the semi-permeable membrane leakage prevention system to be used in other applications. Examples of such other leakage systems include other components that are implanted and/or inserted into a living body where it is desired to prevent blood or other fluid from leaking by passing around the implanted or inserted component.

While various embodiments have been described above, it should be understood that they have been presented only as illustrations and examples of the present invention, and not by way of limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A method of reducing paravalvular leakage from a prosthetic heart valve, wherein the method comprises:
    providing a prosthetic heart valve comprising a stent frame having a surface, a valve structure associated with the stent frame, a sealing mechanism including at least one semi-permeable membrane and an osmotic gradient driving material, wherein the sealing mechanism is positioned at least partially over the surface of the stent frame, wherein the prosthetic heart valve further includes a dissolvable coating layer on the at least one semi-permeable membrane;
    deploying the prosthetic heart valve in a patient, wherein the osmotic gradient driving material causes fluid of the patient to pass through the at least one semi-permeable membrane, wherein the fluid that passes through the at least one semi-permeable membrane causes the sealing mechanism to swell and such swelling reduces paravalvular leakage between the prosthetic heart valve and tissue of the patient;
    exposing the dissolvable coating layer to at least one of blood and a solvent; and
    dissolving the dissolvable coating layer.

2. The method of claim 1, and further comprising sealing the osmotic gradient driving material within the at least one semi-permeable membrane.

3. The method of claim 1, wherein the at least one semi-permeable membrane comprises two semi-permeable membranes and wherein the osmotic gradient driving material is placed between the two semi-permeable membranes.

4. The method of claim 1, wherein the osmotic gradient driving material comprises at least one organic or inorganic compound that is positively or negatively charged.

5. The method of claim 1, wherein the osmotic gradient driving material comprises at least one inorganic salt and at least one charged organic compound.

6. The method of claim 1, wherein the at least one semi-permeable membrane is fabricated from a cellulosic material.

7. The method of claim 1, and further comprising securing the sealing mechanism to the stent frame by at least one of a mechanical fastener and a biocompatible adhesive.

8. The method of claim 1, wherein the stent frame is expandable from a compressed configuration to an expanded configuration and wherein the valve structure comprises at least two leaflets.

9. The method of claim 1, wherein the step of exposing the dissolvable coating layer to at least one of blood and a solvent includes exposing the dissolvable coating layer to blood and a solvent.

10. The method of claim 1, wherein the two semi-permeable membranes include an inner membrane and an outer membrane, and the osmotic gradient driving material is placed between the inner and outer membranes, further wherein the stent frame is positioned between the inner membrane and the outer membrane.

11. A method of reducing paravalvular leakage from a prosthetic heart valve, wherein the method comprises:
    providing a prosthetic heart valve including a stent frame having: a surface, a valve structure associated with the stent frame, and a sealing mechanism, wherein the sealing mechanism includes: two semi-permeable membranes including an inner membrane and an outer membrane, and at least one osmotic gradient driving material placed between the inner and outer membranes, further wherein the stent frame is positioned between the inner membrane and the outer membrane; and
    deploying the prosthetic heart valve in a patient, wherein the osmotic gradient driving material causes fluid of the patient to pass through the two semi-permeable membranes, wherein the fluid that passes through the two semi-permeable membranes causes the sealing mechanism to swell and such swelling reduces paravalvular leakage between the prosthetic heart valve and tissue of the patient.

12. The method of claim 11, wherein each of the inner and outer membranes are made of materials having a molecular cutoff range between 1 and 1,000,000 kilodaltons.

13. The method of claim 11, wherein the prosthetic heart valve further includes a dissolvable coating layer on the outer membrane.

14. The method of claim 13, wherein the method further includes:
    exposing the dissolvable coating layer to blood; and
    dissolving the dissolvable coating layer.

15. The method of claim 13, wherein the method further includes:
    exposing the dissolvable coating layer to a solvent; and
    dissolving the dissolvable coating layer.

* * * * *